United States Patent [19]
Collins et al.

[11] Patent Number: 5,929,337
[45] Date of Patent: Jul. 27, 1999

[54] NON-MECHANICAL CONTACT ULTRASOUND SYSTEM FOR MONITORING CONTENTS OF A MOVING CONTAINER

[75] Inventors: Andrew Peter Collins, Hanwick Park; Steven Mark Dixon, Solihull; Christopher Edwards, Coundon; Stuart Beaumont Palmer, Kenilworth, all of United Kingdom

[73] Assignees: M & A Packaging Services Limited, Worcestershire; The University of Warwick, Coventry, both of United Kingdom

[21] Appl. No.: 08/854,244

[22] Filed: May 9, 1997

Related U.S. Application Data

[63] Continuation of application No. PCT/GB95/02630, Nov. 9, 1995.

[30] Foreign Application Priority Data

Nov. 11, 1994 [GB] United Kingdom .................. 9422800
Nov. 11, 1994 [GB] United Kingdom .................. 9422801

[51] Int. Cl.[6] .......................... G01N 29/18; G01N 29/22
[52] U.S. Cl. ........................... 73/597; 209/590; 73/602; 73/643; 73/628; 73/629
[58] Field of Search ............................ 73/52, 597, 598, 73/599, 600, 602, 620, 622, 643, 624, 625, 627, 628, 629, 644, 657; 209/524, 529, 590

[56] References Cited

U.S. PATENT DOCUMENTS

| | | | |
|---|---|---|---|
| 3,596,501 | 8/1971 | Forry et al. | 73/52 |
| 3,608,715 | 9/1971 | Snyder et al. | 73/52 |
| 3,802,252 | 4/1974 | Hayward et al. | 73/52 |
| 4,182,451 | 1/1980 | Watson | 209/524 |
| 4,187,718 | 2/1980 | Shibasaki | 73/52 |
| 4,223,790 | 9/1980 | Yoshida | 209/590 |
| 4,821,573 | 4/1989 | Nagata et al. | 73/597 |
| 4,864,848 | 9/1989 | Irvine | 73/45.4 |
| 4,952,063 | 8/1990 | Opsal et al. | 356/432 |
| 5,457,997 | 10/1995 | Naruo et al. | 73/643 |
| 5,602,890 | 2/1997 | Gray et al. | 378/57 |
| 5,608,164 | 3/1997 | MacLauchlan | 73/599 |

FOREIGN PATENT DOCUMENTS

| | | |
|---|---|---|
| 0034098 | 8/1981 | European Pat. Off. . |
| 0516956 | 12/1992 | European Pat. Off. . |

*Primary Examiner*—Hezron Williams
*Assistant Examiner*—Rose M. Miller
*Attorney, Agent, or Firm*—John P. White; Cooper & Dunham LLP

[57] ABSTRACT

A non-contact apparatus for monitoring the contents of a container, especially but not exclusively for quality control monitoring purposes associated with high speed packaging processes, comprises a non-contact ultrasound generation member, adapted so as to generate an ultrasound signal within the container (1). A non-contact detection scheme is employed to enable the contents of the container to be monitored by analysing ultrasound signals that have propagated through or round the container (1) either transmitted through or reflected from the containers contents. In use, the apparatus may be adapted to provide information about container fill level (h) or the presence or absence of an insert (14) such as a head forming device by analysing the measured signal profiles generated by a ultrasound detection member (3).

35 Claims, 7 Drawing Sheets

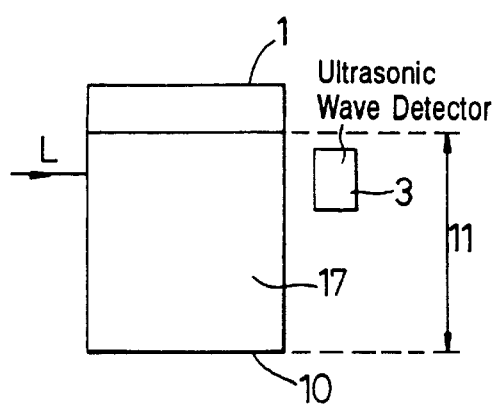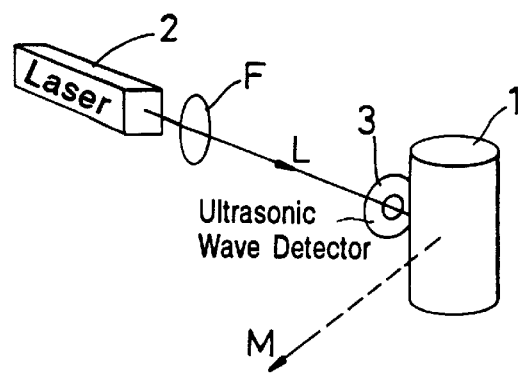
Fig. 3a
Fig. 3b
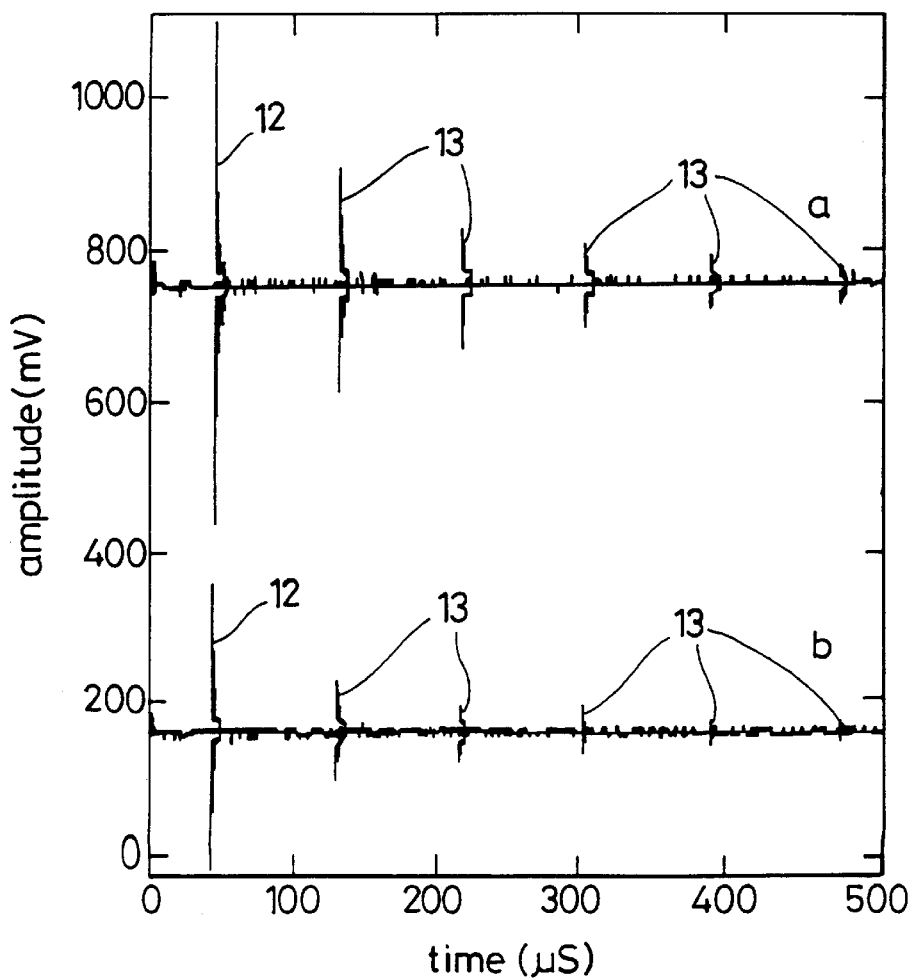
Fig. 4

NON-MECHANICAL CONTACT ULTRASOUND SYSTEM FOR MONITORING CONTENTS OF A MOVING CONTAINER

This application is a continuation of PCT International Application Ser. No. PCT/GB95/02630, with an International filing date of Nov. 9, 1995, designating the U.S. and claiming priority of British Patent Application Nos. 9422800.4, filed Nov. 11, 1994 and 9422801.2, filed Nov. 11, 1994.

This invention relates to non-mechanical contact systems for use in monitoring the contents of containers.

In the packaging industry it is often desirable to provide some means for monitoring the contents of containers on a moving conveyor line, in order to detect, for example, empty containers, or containers whose contents are defective in certain characteristics. In particular, in the beverages packaging industry, it is desirable to be able to monitor the contents of, for example, beverage bottles or cans, on a rapidly moving conveyor line in a bottling or canning plant. More specifically, means are now being sought for detecting a fill level of liquid contents in a sealed bottle or can, for detecting empty cans, and for detecting the presence or absence of head-generating devices or "inserts" (used to simulate draught beer, for example) in filled cans. A system for detecting faulty inserts in filled beverage cans is also desirable.

Previously, non-mechanical contact systems utilising radiation techniques (e.g. gamma radiation or X-rays) have been used to detect fill levels in beverage cans and bottles. Such systems operate on the principle of density gauging. If product is present inside a container at which gamma radiation (or X-rays) is directed, the container is effectively more dense, and hence less radiation is transmitted through the container, than if the product is absent. By positioning a radiation detector at a known height such a system may be used to determine whether or not the container is filled to a predetermined level. However, from a safety point of view, gamma radiation (or X-rays) in the workplace is undesirable, and additionally, significant legislative and cost drawbacks are faced by anyone using gamma radiation or X-rays.

According to a first aspect of the present invention, a non-contact apparatus for monitoring contents of a moving container is provided comprising non-contact ultrasonic wave generation means adapted to product in use an ultrasonic wave in a container being monitored, non-contact ultrasonic wave detector means adapted to detect an ultrasonic signal and to generate a detection signal dependent upon the ultrasonic signal which is detected, and signal processing means adapted to process the detection signal generated by the ultrasonic wave detector means in order to detect a particular characteristic of the contents of the container.

Preferably the wave generation means is adjusted to generate a wave in a moving container.

Preferably the detector means is adapted to detect a signal in a moving container.

Preferably the wave detector means is adapted to detect an ultrasound signal that has propagated through the contents of the container.

Instead of, or perhaps in addition to, detecting a longitudinal bulk wave through the container and its contents we might detect a surface wave in the container, such as a Lamb wave.

The non-contact apparatus of the present invention is advantageous in that it can be used to monitor the contents of containers moving past the apparatus at very rapid velocities. For example, in a beverage can filling line at least 2500 cans may move past the apparatus per minute. Such high velocity container movement means that, in such a beverage can filling line, the total available time for carrying out a monitoring measurement on each can, processing the results of the measurement, and, if necessary, removing the can from the filling line if it is found to be unsatisfactory in some way, is usually only of the order of between 12 and 15 milliseconds. Monitoring the contents of such dynamic targets presents significant problems which the present invention overcomes.

Ultrasonic wave propagation through a container and its contents, and detection of an ultrasonic wave propagating in the container, can take place in a relatively short time due to the nature of ultrasound itself. Theoretically, the velocity of ultrasound waves would enable in the order of up to 100,000 containers to be monitored per minute.

The speed of operation of the present invention may effectively "freeze-frame" the moving containers, the very speed reducing problems associated with moving targets. The realisation that with an ultrasound sensor detecting bulk waves the speed of movement of containers on a filling lines does not really matter is at least in part a factor in the invention.

In the case of Lamb waves the speed of propagation is far lower than bulk wave propagation, and the speed of movement of the filling line may be significant.

There may be other factors which reduce the capability of a checking system (e.g. signal processing time) but theoretically the speed of bulk wave ultrasound is currently not a limiting factor.

In one embodiment of the invention the non-contact wave generation means comprises a laser.

The non-contact wave generation means may comprise plasma-producing means adapted to produce a plasma at or near the surface of a container. The plasma producing means may comprise a laser. Alternatively it could be an electrical source (e.g. high voltage "lighting strike").

The plasma producing means may produce plasma, e.g. by a high energy strike, at the container surface, for example by having a laser or electrical spark hit the container. However, we prefer to have the plasma generated at a region close to the container, but not actually in the wall of the container. Spaced plasma generation means is preferably provided to achieve this. The spaced plasma generation means may comprise a target that is not the container (e.g. a member between the energy source that produces the plasma strike and the container). We may simply have a target plate next to the container, the laser (or other energy source) striking the target plate instead of the container directly.

This plasma ultrasound source is considered to have advantages and may even comprise an invention in its own right.

One advantage of the plasma target system is that we have found that by using plasma to generate ultrasound no mark, or much less of a mark, can be made on the container (direct impact with a laser of sufficient intensity to generate ultrasound can mark the surface of a container). In practice we have found that using plasma to generate the ultrasound leaves no mark.

The laser is preferably adapted to operate in pulsed mode. Pulsed lasers can fire many times per second. This enables us to monitor many containers per second.

The detection signal is preferably an electrical signal. The detection signal may be an electronic signal.

The apparatus preferably further comprises focusing means adapted to focus the beam of laser radiation to a spot on an outer surface of a first portion of the container in order to generate an ultrasonic wave in the container (or focus the beam onto a plasma-generating target). The use of a pulsed laser which is fired many times per second, enables ultrasound signals to be generated in individual containers passing the non-contact apparatus in quick succession. For example, commercially available pulsed carbon dioxide lasers are capable of firing in the order of up to 6000 shots per minute.

One advantage of one embodiment of the present invention is its ability to generate an ultrasonic wave in a portion of the container, which, in turn, transmits the ultrasonic wave to the contents of the container, without the need for direct mechanical contact with the container, or its contents. This enables the contents of sealed containers, moving on a conveyor line, to be freely monitored.

Preferably the ultrasonic wave generated in the first wall of the container is a longitudinal, compressional, wave propagating away from the outer surface of the first portion, and propagating into the contents held in the container. The contents are preferably liquid contents, the term "liquid contents" being herein defined as any substance comprising a sufficient liquid proportion to enable ultrasound to propagate through the substance. For example, the liquid contents may be a slurry.

The detector means may be positioned relative to the container in such a manner that it may detect ultrasonic displacements of the surface/wall of the container.

The detector means may be positioned at any angle relative to a central axis of the container. (For example 0°, 30°, or 45°, 140°, or 180° to the line of sight of ultrasonic generation).

The laser/plasma need not hit the surface of the container normally: a glancing, inclined, orientation will still produce a component of ultrasound in the direction normal to the container surface.

The detector means may further be positioned such that it may detect an ultrasonic wave in a second portion of the container. The second portion may be provided opposite the first portion. In this position, the detector means may effectively detect ultrasound transmitted through the contents of the container. With this detector means arrangement the apparatus operates in what is therefore known as the "through transmission" mode.

Alternatively, the detector means may be positioned such that it may detect an ultrasonic wave in the first portion of the container, or a portion of the container proximal to the first portion, which wave has been reflected from other portions of the container (for example from the second portion of the container) and has propagated back to the first portion of the container, or the portion proximal to the first portion. With the detector means in this arrangement, the apparatus operates in what is known as the "pulse echo" mode. One advantage of the pulse echo mode is that the detector means is positioned to the same side of the container as the laser means. This means that with pulsed echo mode we do not need necessarily to gain access to the far side of the container. (However, it can be easier to gain access to the container using through transmission).

In either of the through transmission mode or the pulse echo mode, the detector means is preferably adapted to detect a number of ultrasonic waves in the container resulting from multiple reflections or "echoes" of the generated ultrasonic wave within the container, and to generate a corresponding detection signal for each such detected ultrasonic wave. Alternatively, we could detect only the first (or a single) signal.

In the through transmission mode the detector means need not be located at one hundred and eighty degrees (with respect to a central axis of the container being monitored) to the portion of the container in which the ultrasonic wave is generated, but may be located at any convenient angle at which transmitted ultrasound may be detected (for example at 45° to the direction of longitudinal ultrasound propagation). Similarly, in the pulse echo mode the detector means need not be located at zero degrees (with respect to the central axis of the container being monitored) relative to the portion of the container in which the ultrasonic wave is generated, but may be located at any convenient angle at which ultrasound reflected from other portions of the container may be detected.

The ultrasonic wave detector means may comprise a permanent magnet and a conductive coil.

Of course, other detectors are possible.

The ultrasonic wave detector means may further comprise a broadband pre-amplifier in electrical or electronic connection with the ultrasound detector.

Alternatively the ultrasonic wave detector means may comprise an optical detection technique.

The signal processing means preferably processes the detection signals so as to determine whether a predetermined characteristic has been achieved. This can be used to provide a yes/no answer. For example, the signal processing means could simply determine whether the container was filled with contents at least to a predetermined level. It might do this simply by seeing whether the magnitude of the (or a selected) detection signal was above or below a predetermined strength, or value.

In more complex systems the signal processing means may be adapted to process the detection signals received from the detector means and to compile a resultant signal profile. The form of this profile is determined by the nature of the contents of the moving container, and may be referred to as the captured ultrasonic "signature" profile of the container contents.

The system may be "taught" the characteristic or profile of an acceptable container by operating it on an acceptable container and recording the acceptable signal value, or profile. An allowable range of acceptable signal values or profiles may be stored. The value or range of values may be input by trials on actual containers.

The apparatus may be adapted to function as a fill level detector for a beverage container. Indeed, this is seen as being a prime use of the apparatus. The apparatus may operate in either the through transmission mode or the pulse echo mode. The apparatus is preferably arranged such that the focusing means (optics in the case of a laser power source) focus the energy output of the energy source (e.g. laser radiation) onto the container (or alternatively onto the target in front of the container) at a pre-determined height above a base of the container, at which height liquid beverage in the container is expected to be present. If the container is filled to this height or level, then a signal profile comprising a strongly transmitted wave (in the through transmission mode) or a strongly reflected wave (in the pulse echo mode), and multiple echoes (in both modes) is captured by the detector means. However, if the container is empty, or filled to a level below the pre-determined height, the captured profile will not have the characteristic longitudinal echo profile (although it will have a strong surface wave signal), since the generated longitudinal ultrasonic wave is not transmitted by air in the container.

Alternatively, the apparatus may be adapted to function as a means for detecting the presence, or absence, of an insert within a liquid-containing beverage can. (The insert may be, for example, a head-generating device or a device for chilling beverage in the can). In the through transmission mode, this may be achieved by arranging the apparatus such that the focusing optics focus the beam of laser radiation onto the can at a chosen height lying between a base of the can and a known maximum height of an insert located correctly in the can. A gas-filled insert present in the can will block any longitudinal ultrasonic wave propagating through the can and its liquid contents at the chosen height, and therefore substantially no longitudinal ultrasonic waves will be detected by the detector means (or a substantially reduced or modified signal). If no insert is present in the can (or is not present in its correct position), the captured ultrasonic wave profile will comprise a transmitted wave.

The apparatus may be adapted to function as a means for detecting the presence or absence of an insert and may be arranged to operate in the through transmission mode. In this mode, and with the focused laser beam (or plasma generation) at the same height as the "widget" is expected to be present, if a test can contains an insert the detector means detects a signal arising from ultrasound transmitted through the liquid contents of the can and subsequently blocked by the insert. If no insert is present, the signal value for a "normal" liquid-containing can is obtained. Alternatively we may prefer to detect the presence of structures in containers using pulse echo mode detection. One advantage of operating the insert detection apparatus in the pulse echo mode is that the pulse echo mode provides a positive signal test. In the transmission mode, the apparatus interprets a zero signal as indicating the presence of an insert. However, such a zero signal could also be produced by an empty can, or even faulty test equipment, and so is not necessarily conclusive as an indication that the can is acceptable.

The apparatus may be able to detect the difference between two different kinds of insert. The apparatus additionally or alternatively may be further adapted to detect the presence or absence of a central tube or straw in a test can. This may, for example, be a vent or filler tube which has been deposited inside the can during filling and which may be in a central position within the contents of the can. By arranging the apparatus such that the ultrasonic wave is generated at a height above a lower end of the tube but below an expected maximum height of the tube, the presence of the tube can be detected, as either blocking of ultrasound in the through transmission mode, or as multiple echoes arising from ultrasonic wave reflections off the tube in the pulse echo mode.

By storing suitable pre-programmed reference characteristics (e.g. data on velocity and temperature) in the memory of the signal processing means, the apparatus may be adapted to detect a pre-determined temperature of the contents of the container, or an expected solid to liquid ratio of the contents, or to detect an empty container.

According to a second aspect of the invention we provide a container filling line comprising a filling station; conveyor means for moving containers past the filling station; inspection means including non-contact monitoring means; and control means; the arrangement being such that the control means controls in use the operation of the filling line in response to signals from the monitoring means, and in which the monitoring means comprises apparatus in accordance with the first aspect of the invention.

The container filling line or inspection means may further comprise container rejection means arranged such that the control means controls in use the operation of the container rejection means in response to signals from the monitoring means so as to remove containers assessed by the control means to be not acceptable.

Preferably the container rejection means comprises a pneumatic device adapted to remove a container from the conveyor means. Alternatively, the rejection means may comprise electromagnetic means, servo-controlled impact means, or hydraulic means.

Instead of, or in addition to, rejection means the line may have marking means adapted to mark the container with a mark dependant upon the signals received. The mark may be a quality control mark. It may be made by a laser, preferably the same laser that generates the ultrasound. The laser may fire twice, once to generate ultrasound and once to mark the container as having been tested, or with, for example, a pass/fail mark. The mark may be non-symmetrical, and may be made using a mask. The quality control mark may be the mark made by the ultrasound generating pulse. This feature of the marking means may be a separate invention.

The control means may also control the filling of a container at the filling station and/or the speed of the conveyor means. There may be feedback from the monitoring means to the control means which is used to control the filling of the containers. Thus the monitoring means may not only monitor whether the filled containers are acceptable, but may also provide an input signal in the control of a filling dispenser of the filling station and/or the speed at which containers are presented to the filling dispenser.

The feedback is preferably negative feedback, but it may be positive feedback.

It will be appreciated that the laser axis need not necessarily be radial in relation to a cylindrical container. It could be in a direction parallel to the axis of a container, or at some other angle.

According to a third aspect of the invention we provide as a kit adapted to be fitted to a container filling line monitoring apparatus in accordance with the first aspect of the invention.

The kit preferably also has signal processing means.

According to a fourth aspect, the present invention provides a non-contact method of monitoring contents of a moving container comprising, firstly, generating an ultrasonic wave within a portion of the container, secondly, detecting an ultrasonic signal in a portion of the container and producing a detection signal dependent upon the detected ultrasonic signal, and thirdly processing the detection signal in order to detect a particular characteristic of the contents of the container.

Preferably the method further comprises the step of allowing the ultrasonic wave generated to propagate through the contents of the container before it is detected.

The method may comprise detecting a reflected ultrasonic signal (pulse echo detection). Alternatively we may detect the through signal.

Preferably the ultrasonic wave is generated by the impact of a laser beam or by a plasma generating device adapted to generate plasma slightly spaced from the container.

Preferably the detection signal is an electrical or electronic signal.

According to another aspect the invention comprises a can or other container that has been monitored or inspected using the method or apparatus of a preceding aspect of the invention.

The non-contact method may further comprise the steps of emitting further signal beams of laser radiation in order to generate further ultrasonic waves in one or more portions of the container, and separately detecting ultrasonic signals in the container corresponding to respective generated waves in order to substantially simultaneously detect a number of characteristics of the contents of the container.

The invention may be considered, looked at in one way, to be the use of an ultrasound signal that has been propagated through the contents of a moving container in assessing whether the filled container meets desired standards, or in controlling a filling line.

As mentioned earlier, the concept of generating plasma before the article to be tested may comprise a separate invention.

According to another aspect of the invention we provide an ultrasound source comprising an energy source adapted to produce a burst of energy and a plasma-generating target, the arrangement being such that in use the target is interposed between the energy source and an article that is to have ultrasound generated in it, and the energy source produces in use an energy strike that impinges on the target, as opposed to impinging directly on the object, the target producing a burst of plasma which generates ultrasound in the article.

The target is preferably spaced from the article. The spacing may be of the order of 1 mm, 2 mm, 3 mm, 4 mm, 5 mm, or above.

The target may be moveable. It may be replaceable.

Focusing means may be provided to focus the energy strike onto the target. The energy source may be a laser.

We may provide a non-contact inspection or checking apparatus that includes an ultrasound energy source in accordance with the above aspect of the invention.

Embodiments of the invention are illustrated in the accompanying drawings in which:

FIG. 2b is an end view of the ultrasonic wave detector of FIG. 2a;

FIG. 3a is a schematic illustration in cross section of a fill level detector according to an embodiment of the invention operating in a "through transmission" mode;

FIG. 3b is a schematic illustration in perspective view of a fill level detector according to an embodiment of the invention and operating in a "pulse echo" mode;

FIG. 4 shows two captured signal profiles obtained from the fill level detector in the transmission mode, following two laser shots, a, b;

Figure 1:
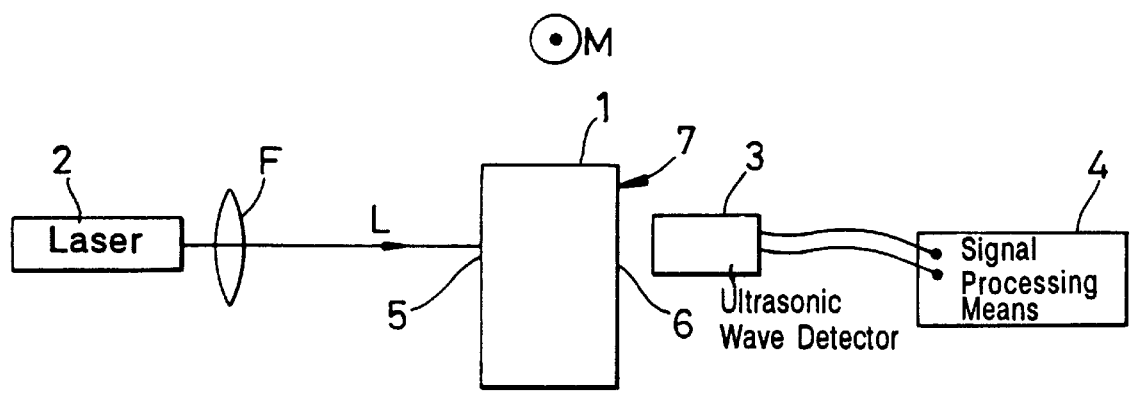
FIG. 1 is a schematic illustration of a side view of an embodiment of a non-contact apparatus for monitoring the contents of a moving container.

FIG. 1 illustrates schematically a non-contact apparatus for monitoring the contents of a moving container 1 which is, in the illustrated embodiment, a metal (e.g. steel or aluminium) beverage can of generally cylindrical shape. The apparatus comprises a laser 2 which operates in a pulsed mode, focusing optics F, comprising one or more lenses arranged to focus a laser beam L emitted by the laser to a spot on a portion 5 of an outer surface 7 of the can 1, an ultrasonic wave detector 3, and signal processing means 4.

As shown in FIG. 1, the can 1 is moving in a direction M (out of the page) on a conveyor line carrying many such cans. In an alternative arrangement, the can is, for example, suspended from, or attached to, a moving conveyor.

In the embodiment illustrated in FIG. 1, the focused laser beam L propagates along an axis perpendicular to the portion of outer surface of the can upon which the laser spot impinges, and the detector 3 is coaxially aligned with the focused laser beam but is located proximate to a portion 6 of the surface 7 of the can directly opposing the portion 5, in order to detect ultrasound transmitted through the can 1.

In this embodiment the laser is a Q-switched Neodymium (Nd:YAG) laser having a rise time of 5 ns and 1.06 $\mu$m radiation wavelength with a corresponding energy of 80 mJ. Any laser suitable for generating ultrasound could, of course, be used. The focusing optics focuses the emitted beam to a spot size of approximately 1 mm diameter on the outer surface 7 of the can. The focused spot of laser radiation concentrated on the surface of the can ablates approximately one micron of the surface, thus creating a reactive force in the can, which causes a short ultrasonic pulse in a wall of the can which comprises the surface portion 5.

Where damage to the surface of the can is not desirable we can reduce it, or avoid it, by using a suitable coating, such as a lacquer. This may be sacrificial, or resistant to damage.

In a preferred alternative embodiment for use with unpainted or uncoated cans, the laser is a pulsed carbon dioxide ($CO_2$) laser. In one embodiment, the $CO_2$ laser has a 2J pulse energy, 50 ns pulse width at half height, beam dimension of 16×16 mm, and a wavelength of 10.6 $\mu$m. $CO_2$ radiation is not well absorbed by a metal can (at this wavelength most metals are almost perfect mirrors), but on reflection from the can it generates a plasma in air at the surface of the can. Ultrasound generation occurs via this air breakdown mechanism, when air expands at supersonic speeds and pushes against the can surface creating strong ultrasonic waves in the can (this is direct laser hit).

In either embodiment, the laser may effectively remove a disc of paint of approximately 1 mm diameter from the surface of the can. Alternatively, the laser may remove paint from the can surface in order to leave a predetermined shape e.g. a tick, which may then perform as a quality control mark on the can surface. The shape of the mark could be determined by a mask, for example.

The ultrasonic waves generated in the can comprise longitudinal (or compressional) ultrasonic waves propagating in a direction generally perpendicular to the portions 5, 6 of the surface 7 of the can. Longitudinal ultrasound of more than a few hundred KHz (the ultrasound in which we are usually interested) propagates over many centimeters in metals and liquids, but is not transmitted strongly in gas e.g. air. In addition, at a boundary between these materials a proportion of the energy of the ultrasound is reflected and very little is transmitted. For example, and without suggesting that the following figures are anything more than illustrative possibilities, at a "can to liquid" interface, approximately 80% of the energy might be reflected in the can and approximately 20% will be transmitted to the liquid interface. However, at a "can to air" interface, 99.99% of the energy might be reflected in the can with only 0.01% being transmitted to the air. Consequently, only 0.01% of the energy in an ultrasonic wave generated in a portion of the can when the can 1 is empty of liquid (and contains only air) will be transmitted to the air inside the can and the amount of energy subsequently transmitted to an opposing portion of the can by the air will be substantially zero, given the initial energy of the ultrasound generated by the focused laser beam. However, if the can contains liquid up to a height at or above the height at which the focused laser spot impinges on the can a substantial amount of the generated ultrasonic energy will be transmitted through the can by the liquid contents of the can. Additionally, since the ultrasonic wave is partly reflected at the opposing portion of the can, a number of reflected waves or "echoes" are present in the can itself, and its contents, as the wave effectively bounces from one side of the can to the other, losing energy in the process and eventually decaying.

Figure 2A:
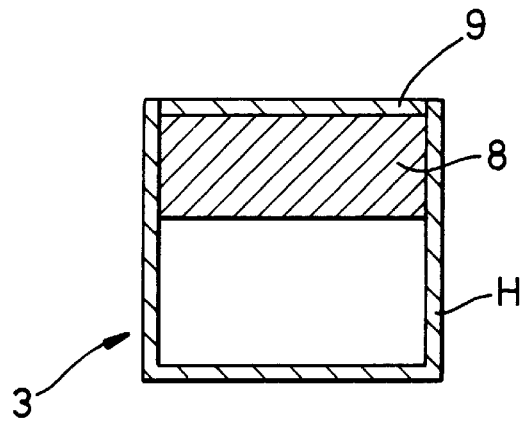
FIG. 2a is a cross-sectional side view of an ultrasonic wave detector incorporated in the non-contact apparatus of one embodiment of the invention.
Figure 2B:
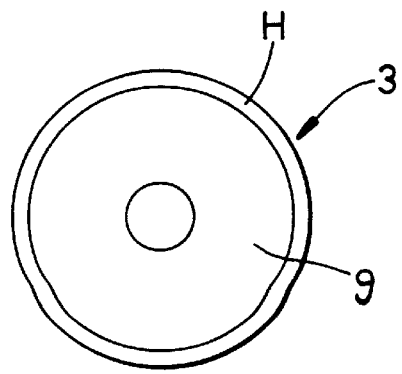

In the embodiment illustrated in FIGS. 1, 2a and 2b, the ultrasonic wave detector 3 is an electromagnetic acoustic transducer (EMAT). The EMAT is a broadband non-contact sensor of acoustic waves in metals and it comprises a permanent magnet 8 faced by a conductive coil 9, housed in a housing H. The EMAT can be used both to generate and to detect ultrasound, but in this specific embodiment does not generate ultrasound sufficiently strong for use as a ultrasound generator in non-contact apparatus according to the present invention. (However, it is envisaged that future improved EMATs or other transducers may be capable of generating sufficiently strong signals for such purposes. An EMAT may indeed be the ultrasound generation means). The EMAT acts as a detector by detecting surface movement of the surface 7 of the can which is vibrating ultrasonically. The interaction of the movement of the metal can with the magnetic field from the EMAT induces a current in the can which in turn induces a current in the conductive coil 9 of the EMAT. In this embodiment, the EMAT detector is optimised to detect longitudinal ultrasonic waves. The EMAT could also be optimised for detection only (i.e. not generation) of ultrasound, which would increase its sensitivity.

If the container 1 being monitored is not a metal container, the laser 2 will still generate ultrasound in the container, but in this case the detector 3 comprises an optical sensor or an air-coupled transducer (ACT) which is capable of detecting ultrasonic vibrations of the can via vibrations transmitted to the air surrounding the can.

Although the EMAT detector may be positioned at any given angle lying between zero and one hundred and eighty degrees to the focused laser beam, our preferred arrangement is to have through transmission at around the straight-through position.

In the embodiment illustrated schematically in FIG. 1, the detector is positioned such that the can lies between the laser 1 and the detector 3 such that the detector may detect ultrasound transmitted through the container, from the portion upon which the focused laser beam impinges to an opposing portion of the container proximate to the detector. In this arrangement the apparatus will henceforth be referred to as operating in the "through" transmission mode.

In a preferred embodiment, the detector 3 further comprises a broadband pre-amplifier, sometimes in conjunction with a filter (e.g. band pass filter) which filters electrical signals leaving the detector before they are fed to the signal processing means 4 in order to optimise signal to noise ratio.

The surface of the EMAT may comprise an absorbent non-conducting material, which reduces pick-up signals from airborne ultrasound.

In an alternative embodiment (not shown) the ultrasonic wave detector is an optical device, possibly a laser interferometer, arranged so as to detect surface movement of the surface 7 of the can caused by ultrasound through the can.

In one embodiment, the non-contact apparatus functions as a fill level detector for use in detecting a pre-determined level of liquid in a container 1. The apparatus is arranged to operate in the through transmission mode, with a focused Nd:YAG laser beam L impinging on the surface of the container at a height which is just below (i.e. approximately 0.5 mm below if the focused laser spot is approximately 1.0 mm in diameter) an expected fill height or level 11 of liquid contents 17 of the container, relative to a base 10 of the container, as shown schematically in FIG. 3a. If the container is filled to the expected fill level, the EMAT detects a series of ultrasonic waves as shown in FIG. 4, which is a plot of the detected voltage in the coil of the EMAT, against time, obtained from the signal processing means.

A TEO $CO_2$ laser could also be used.

The graph shows a captured signal profile a, obtained following a first shot of the pulsed laser, and a captured signal profile b, obtained following a second shot. The large spike 12 in each profile is due to the portion of the incident ultrasonic wave which propagates through the container via the liquid contents of the container without being reflected. The subsequent spikes, or echoes, 13 are due to reflections (or reverberations) of the initially generated wave off interior surfaces of the container. The signals detected following the second shot of the laser, which was focused to a spot covering the same area of the container surface as the focused spot of the first shot, is weaker since the first shot has already ablated some surface coating from the container.

A profile exhibiting multiple echoes 13 can effectively act as a signature profile for a can containing liquid substantially up to the expected fill level. If the can is not substantially filled up to the expected fill level, then the generated longitudinal ultrasound will not be transmitted through the container and substantially no signal indicating through transmission of ultrasound will be detected by the EMAT. A signal may be detected but this is due to an ultrasonic surface wave in the surface of the container, rather than a longitudinal (compressional) wave.

In one possible embodiment, the fill level detecting apparatus is arranged such that the EMAT detector is positioned between the laser and the container, so that the incident focused laser beam L passes through the centre of the doughnut-shaped detector 3 prior to impinging upon the surface of the container. This arrangement is illustrated schematically in FIG. 3b. In this position, the first ultrasonic wave detected by the EMAT is due to the first reflection of the generated wave off the wall of the container which comprises the surface portion 6, located on a far side of the can relative to the laser 2. A series of multiple echoes due to further reflections within the container will be detected, as in the through transmission mode. With the detector positioned in this manner, the apparatus will henceforth be referred to as operating in the "pulse echo" mode. An advantage of the pulse echo mode is that access is required to one side of the container only, the laser and detector do not have to be located on opposite sides of the container being monitored.

In the described embodiments, the signal processing means comprises a personal computer incorporating signal processing software. However, any central processing unit (CPU) capable of performing the necessary calculations could be used. A threshold value for the received signal is stored by the CPU and the received signal is compared with this threshold value in order to determine whether the test container is filled to the expected or required fill level.

In a further embodiment of the invention the computer is programmed to activate a removal device when an empty can, or a "faulty" can is detected, and the activated removal device removes the can in question from the moving conveyor line. The removal device is a pneumatic device in this embodiment, but in further alternative embodiments may be a servo-controlled impact device, or a device operating on electromagnetic or hydraulic principles. The removal device will almost invariably includes a tracking system to enable an empty, partially filled, or faulty can to be detected at one region of the filling line and removed at another region downstream.

Figure 5:
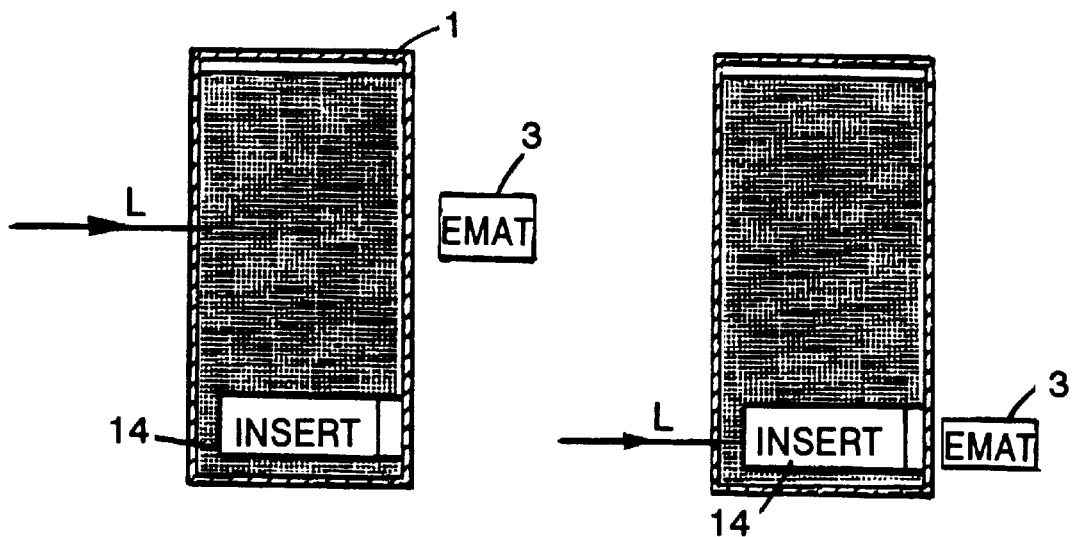
FIG. 5 is a schematic illustration in cross section of an "insert" detection apparatus according to an embodiment of the invention.
Figure 6:
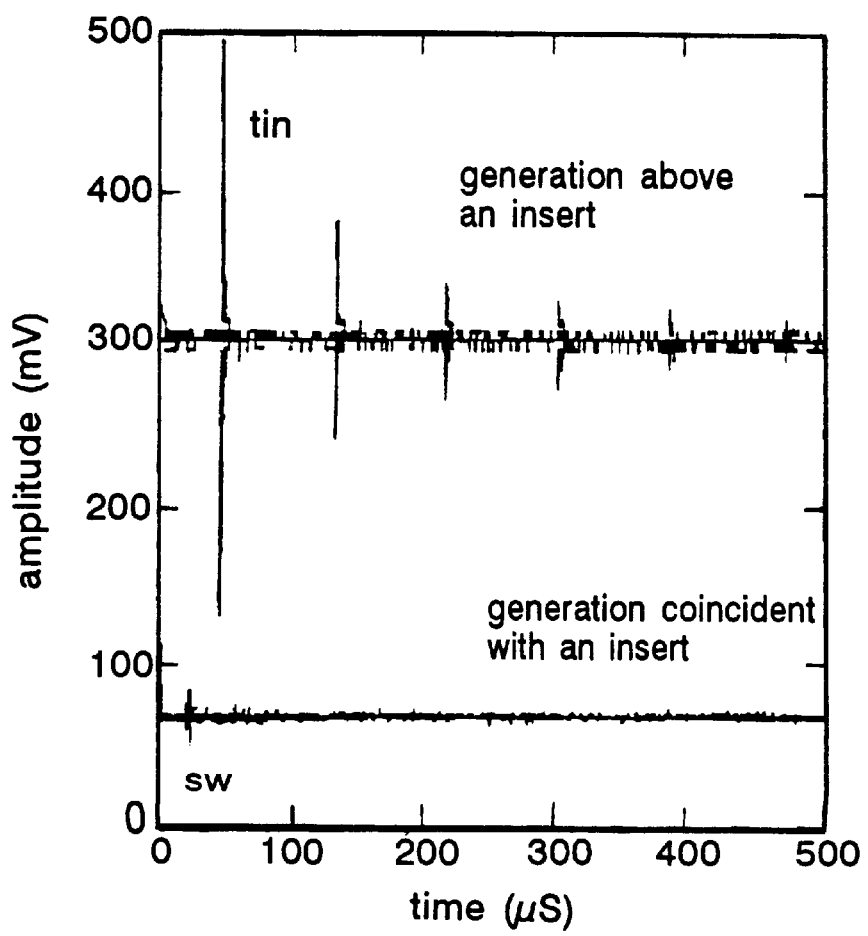
FIG. 6 shows two captured signal profiles obtained when an Nd:YAG laser is focused above, or coincident, with a widget in a liquid-containing can.

In a still further embodiment of the invention, the non-contact apparatus may operate as a means for detecting the presence of a head-generation device or insert 14 which may be, for example, a head-generating insert, located at a specified position inside a sealed can substantially filled with a liquid beverage. In this embodiment the apparatus may be operated in either the through transmission mode or the pulse echo mode. The best mode of operation can be dependant on the design of the "widget" that is being looked for. In either mode, the focused laser beam L is directed to a height above the base 10 of the can coincident with the insert 14 located at a specified correct position within the can, as illustrated in FIG. 5. Since the insert prevents the generated ultrasonic wave from being transmitted through the can (especially when the insert is filled with gas), substantially no longitudinal ultrasound will be detected by the EMAT in the through transmission mode as shown in FIG. 6. (A signal SW due to a form of surface wave in the can may still be detected). However, such a "zero signal" could be due not only to the presence of an insert, but also to an empty can, or even faulty test equipment. It may therefore be preferable to operate in the pulse echo mode, for insert detection. In the pulse echo mode, the EMAT will detect at least one ultrasonic echo due to the generated wave being reflected off the insert, back towards the detector. The pulse echo mode thus provides a positive, rather than a negative, signal test.

FIG. 5 further illustrates the case where the focused laser spot impinges on the can at a height lying above the maximum expected height of the correctly positioned insert, with the EMAT positioned in the through transmission mode. As shown in the upper profile in FIG. 6, the captured profile is similar to the "signature" profile for a can substantially filled with liquid and containing no insert. This latter profile would of course be obtained during testing for the presence of an insert, if not insert was present in the can of liquid.

Figure 7:
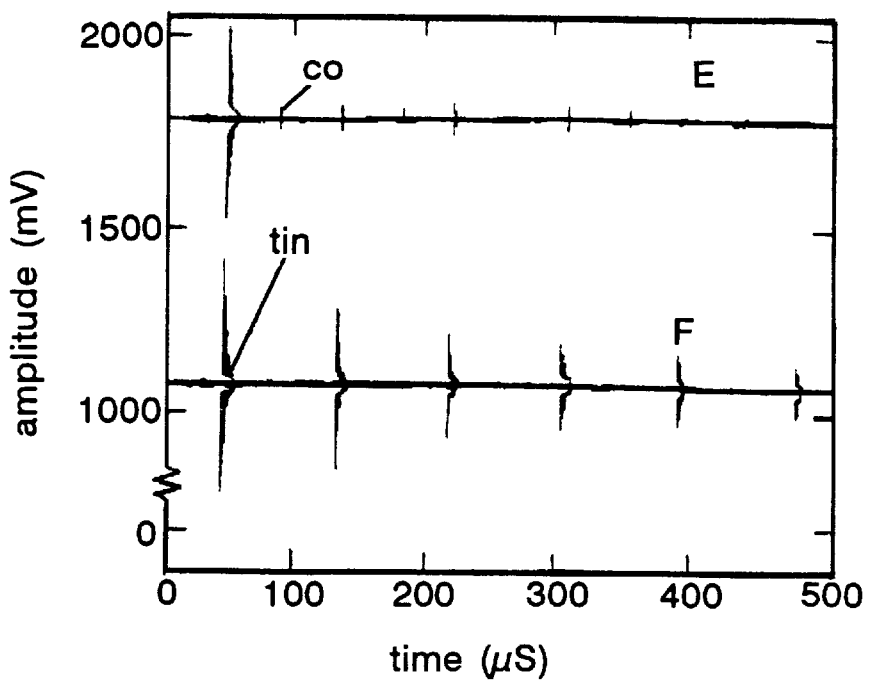
FIG. 7 shows the captured signal profiles obtained in the through transmission mode when a $CO_2$ laser is focused on a can containing a central tube, and a can with no central tube, respectively.
Figure 8:
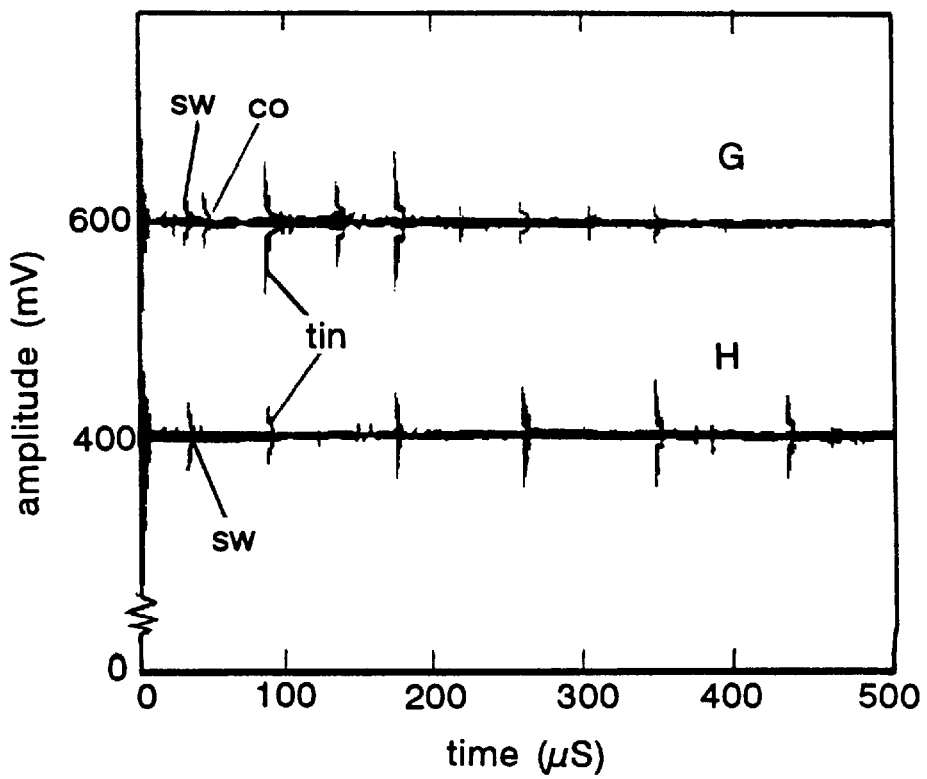
FIG. 8 shows the captured signal profiles obtained in the pulse echo mode when a $CO_2$ laser is focused on a can containing a central tube, and a can with no central tube, respectively.

FIG. 7 illustrates two signal profiles obtained in the transmission mode, using a $CO_2$ laser instead of a Nd:YAG, for test cans having a central tube (profile E), and having no tube (profile F). CO is due to a reflection from the central tube 15, while the multiple echoes shown in profile F are from the interior surface of the can only. FIG. 8 illustrates the corresponding profiles G and H obtained with a $CO_2$ laser, operating the apparatus in the pulse echo mode.

With appropriately designed software and hardware, the non-contact apparatus is capable of monitoring moving cans at a rate determined by the repetition rate of the laser. With commercially available $CO_2$ lasers, the maximum repetition rate would be in the order of 6000 cans per minutes. (The ultimate maximum repetition rate is determined by the time of travel of the ultrasound itself, which sets the limit in the order of 100,000 cans per minute). The fact that the can is moving presents no specific difficulties: a can moving at 5 meters per second will travel a maximum distance of only 0.2 mm during one complete measurement i.e. from firing the laser shot, to capturing the signal profile with the EMAT detector.

It is envisaged that a utopian apparatus could combine insert detection with fill level detection using two or more laser shots fired in quick succession. Additionally, by storing appropriate threshold value, or captured signal profiles in the computer memory, it would be possible to use the non-contact apparatus to also detect a pre-determined temperature of the contents of the container, an expected solid to liquid ratio of the contents, debris (as aforementioned) or contamination in the container, or to simply detect empty containers; or any combination of the features recited. The signal processing software would be capable of comparing one or more captured signal profiles obtained from a succession of laser pulses, in order to substantially simultaneously (i.e. within milliseconds) detect one or more of the expected characteristics of the contents of the can.

Figure 9:
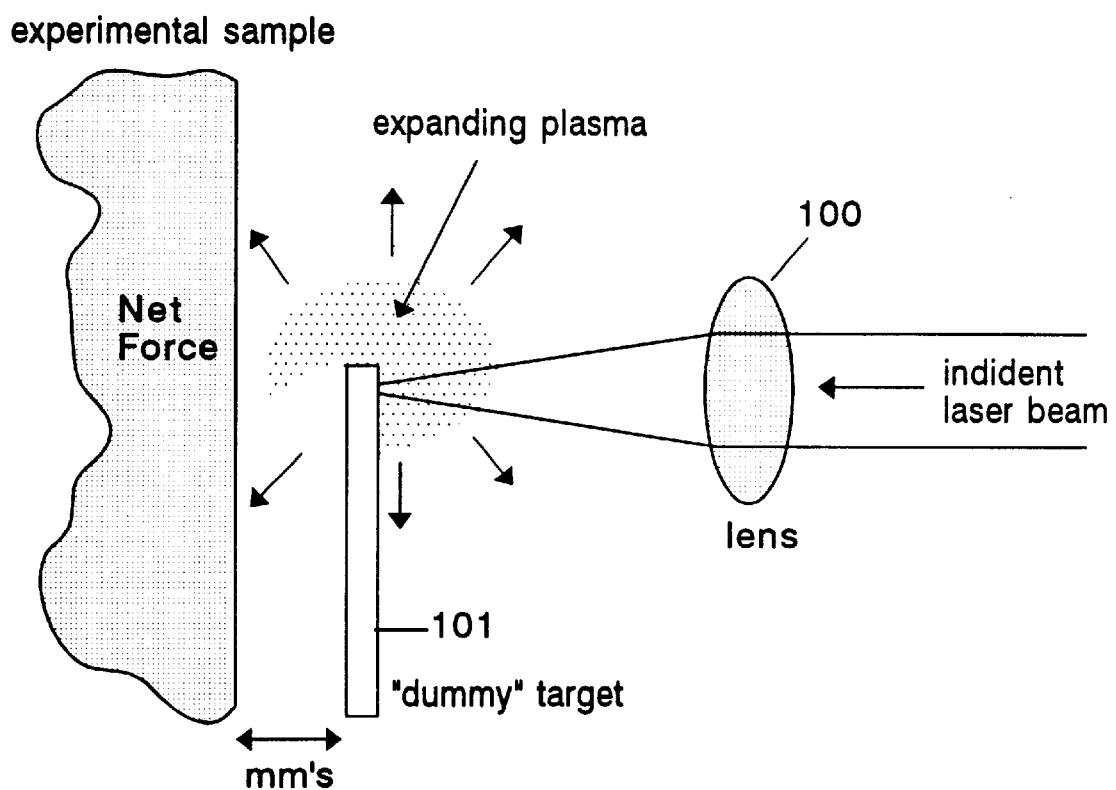
FIG. 9 shows schematically another way of generating ultrasound.

FIG. 9 illustrates another important feature. Instead of having the laser beam (or electrical strike) hit the container directly we have discovered that it can be better to hit a target just before the article being tested. This can help to avoid, or reduce, marking the article.

In order to generate ultrasound in a material, the material must be 'shocked' or stressed. The frequency content of the ultrasound generated will be governed by the rate at which such a stressed state is achieved. For example a periodic mechanical shock of time period one microsecond would generate an ultrasonic wave predominantly of frequency one megahertz. The frequency content of a spike-like ultrasonic generation mechanism contains a range of frequencies and is termed broadband. Making the generating spike sharper in time domain relatively increases the magnitude of the higher frequency ultrasonic components in the resulting ultrasonic wave.

Pulsed lasers can be used to generate ultrasonic waves by rapidly stressing the surface or surface layer of a sample when directed onto that sample. If the laser is of sufficient energy density at the sample surface it can generate a plasma, which may comprise particles that have derived from the sample surface and the surrounding atmosphere at that point. This plasma has a net resultant force normal to the surface of the sample and thus predominantly generates a longitudinal wave in the sample. This mode of laser generated ultrasound is said to be in the ablative regime. At low laser energy densities the illuminated area of the sample undergoes a rapid heating, and the ultrasound mode generated is predominantly a shear wave mode.

The high energy density required to form a plasma on a sample surface usually requires the incident pulsed laser beam to be focused. One problem with this type of ultrasonic generation of longitudinal waves is that the surface of the sample may absorb significant amounts of the incident energy and be in some way damaged. This would be the case for instance when a TEA $CO_2$ laser is focused onto a painted metal surface, where the paint would be damaged or removed from the surface.

A technique of using the force from the plasma to generate ultrasound without damaging the sample surface has been developed. The technique exploits the fact that a plasma is a hot expanding gas, and directs the plasma onto the experimental sample surface without exposing that surface to the laser beam. This is achieved by generating the plasma on a 'dummy' target in front of or close to the experimental sample in which the ultrasound is to be generated.

FIG. 9 shows a laser beam focused by a lens 100 onto a 'dummy' target 101 in front of the sample (or article) being tested. The laser beam is thus totally blocked from the experimental sample. The laser beam generates a plasma 102 at the target 101. The plasma is free to expand away from the point of impact on the 'dummy' target and impacts on the experimental sample. Thus only the plasma is incident on the surface where ultrasound is to be generated. This technique will predominantly generate longitudinal ultrasonic waves. A metal (eg steel) target of less than 10 mm thick (eg 5 mm) spaced about 3 or 4 mm from the sample is preferred.

We believe that satisfactory results can be achieved with a target—sample spacing in the range >0 mm to 10 or 20 mm, most preferably in the range 1 mm to 5 mm.

The thickness of the target is in part determined by the laser, but about 1 mm thick (or 0.1 to 1 mm thick) is preferred.

The target may be destroyed by the laser (or a hole made in it). This may mean that the target has to be moved between laser strikes to interpose a different part of the target, or different target. The target may be capable of obstructing direct impact from the laser for 2 or 3, or more strokes, producing an acceptable plasma. If so it may not need moving between every strike.

So far we have used bulkwaves through the contents of the container, but we could use surface waves in the container itself, or in a layer of its contents near its walls.

According to another aspect of the present invention, a non-contact container fill level monitoring means comprises non-contact ultrasonic wave generation means adapted to produce in use an ultrasonic Lamb or plate wave in a container being monitored, and non-contact ultrasonic wave detector means adapted to detect an ultrasonic Lamb or plate wave propagating in a wall of the container and to generate at least one detection signal dependent upon the ultrasonic wave which is detected.

Preferably the wave generation means and/or detector means is adapted to generate a wave in a moving container.

The detector means may be adapted in use to generate a series of detection signals, each detection signal in the series being dependent upon the ultrasonic Lamb or plate wave which is detected at a corresponding portion of the wall of the container. The monitoring means may further comprise signal processing means adapted to process the series of detection signals in order to determine quantitatively the height of an upper surface of liquid contents of the container relative to the base of the container. This height can be considered to be the "fill level" of the container.

Alternatively, the detector means may be adapted to detect in use an ultrasonic Lamb or plate wave propagating in a wall of the container at a predetermined height above a base of the container. The predetermined height may be an expected fill level of the contents of the container being monitored. If the container is filled up to this height then a predetermined detection signal is preferably generated by the detector means. In this manner, the monitoring means may function as a fill level detector.

The monitoring means may further comprise focusing optics which focus a beam of laser radiation onto an outer surface of a wall of the container (or onto a dummy target adjacent to the wall) in order to generate a Lamb or plate wave in the wall of the container. The focused signal beam may impinge on the outer surface of the container wall at any height between the base of the container and an expected container fill level, but preferably impinges near the base of the container.

However, if the container contains an insert attached to any wall of the container, the focused signal beam preferably impinges on the container wall at a height lying above the maximum height of the insert in the container.

The ultrasonic wave detector means of the fill level monitoring means according to the first aspect of the invention may comprise an array of ultrasonic wave detectors disposed in a generally vertical arrangement such that the Lamb or plate wave propagating up the container wall is detected at a series of heights lying between the base of the container and an upper end of the container. Each detector which detects the Lamb or plate wave preferably generates a detection signal dependent upon the wave which is detected. Each detection signal is preferably input to the signal processing means.

The signal processing means may comprise a memory in which the height, relative to the container base, of each ultrasonic wave detector in the array of detectors is stored, and the processing means preferably processes the detection signals it receives from the ultrasonic wave detectors in order to determine which detector is positioned at a height which is level with the upper surface of liquid contents of the container. The array may comprise a sufficiently large number of detectors in order that at least one of the detectors is located at a height which is substantially equal to the fill level.

Each ultrasonic wave detector in the array may comprise an electromagnetic acoustic transducer (EMAT).

Alternatively, the ultrasonic wave detector means may comprise a single ultrasonic wave detector. The single detector may be an electromagnetic acoustic transducer (EMAT).

The single ultrasonic wave detector may be located at any angle relative to a central axis of the container. (For example, 30°, 40° or 45° to the propagation axis of the impinging laser beam). Preferably, the detector will be located at 180 degrees relative to the propagation axis of the impinging laser beam.

Alternatively, the ultrasonic wave detector means may comprise an optical device such as a laser interferometer.

According to a second aspect of the invention we provide a container filling line comprising a filling station; conveyor means for moving containers past the filling station; non-contact monitoring means; and control means; the arrangement being such that the control means controls in use the operation of the filling line in response to signals from the monitoring means, and in which the non-contact monitoring means comprises non-contact container fill level monitoring means in accordance with the first aspect of the invention.

According to another aspect of the present invention, a non-contact method of monitoring a liquid fill level in a container comprises, firstly, generating an ultrasonic Lamb or plate wave in a wall of a container being monitored, secondly, detecting the Lamb or plate wave in the container wall and producing at least one detection signal which is dependent upon the Lamb or plate wave which is detected, and thirdly, processing the detection signal in order to determine whether it meets predetermined requirements.

Figure 10:
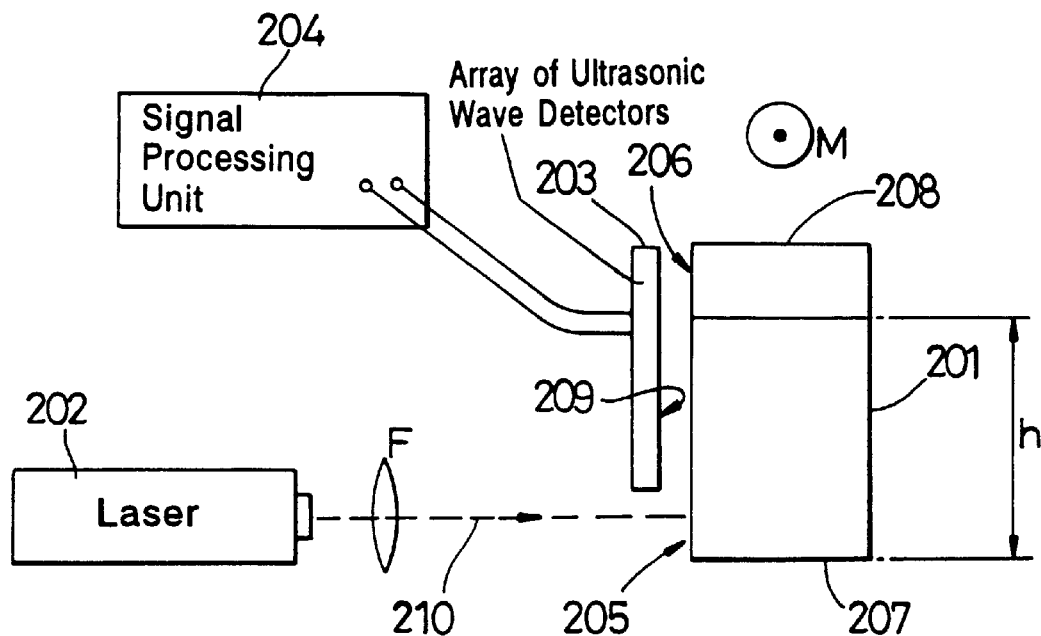
FIG. 10 is a schematic illustration of a side view of another embodiment of a non-contact container fill level monitoring means in use, with the container shown in cross-section.

FIG. 10 illustrates schematically a non-contact container fill level monitoring means in use in monitoring a container 201 which is, in the illustrated embodiment, a metal (e.g. steel or aluminium) beverage can of generally cylindrical shape. The apparatus comprises a laser 202 which operates in a pulsed mode, focusing optic F, comprising one or more lenses arranged to focus a laser beam emitted by the laser to a spot on a portion 205 of an outer surface 206 of the can 201, and ultrasonic wave detector means which is, in the illustrate embodiment, an array 203 of ultrasonic wave detectors. Each of the detectors in the array 203 is electrically connected to a signal processing unit 204.

The can 201 is moving on a conveyor line carrying many such cans. In an alternative arrangement, the can is, for example, suspended from, or attached to, a moving conveyor. The can may be sealed closed, or may still be open.

In the embodiment illustrated in FIG. 10, the can is travelling in a generally transverse direction M (out of the page) relative to the detector array 203 and the focused laser beam propagates along an axis which is generally perpendicular to the transverse direction of travel of the can such that, in use, the propagation axis of the focused laser beam is generally perpendicular to the portion 205 of the outer surface of the can upon which the focused laser spot impinges.

In this embodiment the portion 205 of the outer surface of the can is located proximal to a base 207 of the can, but could be located at a greater height above the base of the can.

The array 203 of detectors is located above the propagation axis of the focused laser beam and comprises a number of detectors which are arranged, in use, substantially in a plane parallel to a central, generally vertical, axis of the can 201 and substantially perpendicular to the propagation axis of the focused laser beam.

The ultrasonic waves generated in the wall of the can in either of these embodiments comprise two types of wave; longitudinal, or compressional, waves propagating within and through the wall in a direction generally parallel to the focused laser beam axis and generally perpendicular to the surface portion 205 of the can 201, and Lamb or plate waves propagating within the wall in a direction generally perpendicular to the focused laser beam axis.

The presence of liquid contents inside the can is believed to modify the Lamb waves propagating in the can wall relative to a Lamb wave travelling up the wall of an empty can. The liquid/air interface in the can effectively creates an effective interface in the side wall of the can which causes reflections of ultrasound waves. Modification of the Lamb wave in the wall of a can containing liquid may be detected, for example, as a difference in amplitude of a Lamb wave detected at a height lying between the base of the can and the height h of an upper surface of the liquid contents of the can, and the amplitude of a Lamb wave detected at a height which lies between the upper surface of liquid and the upper end 208 of the can (the portion of the interior volume of the can located between these two heights being filled only with air, which may be pressurised air). By detecting the amplitude of the Lamb wave at appropriate heights relative to the container base 207, the height h of the upper surface of liquid can be determined. This height h can be considered to be the "fill level".

In the embodiment illustrated in FIG. 10, the detector array 203 comprises a number of electromagnetic acoustic transducers (EMATs).

If the container 201 being monitored is not a metal container, the laser 202 will still generate ultrasound in the container, but in this case each detector in the array 203 comprises an air-coupled transducer (ACT) which is capable of detecting ultrasonic vibrations of the can via vibrations transmitted to the air surrounding the can.

Figure 11A:
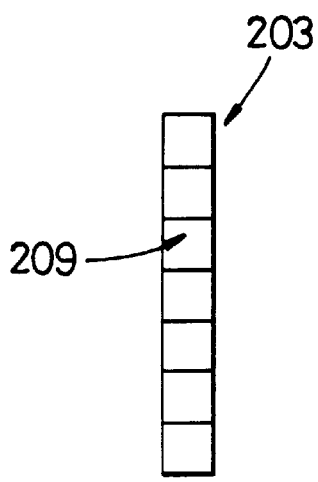
FIG. 11a is a schematic illustration of an ultrasonic wave detector array incorporated in a non-contact fill level monitoring means according to one embodiment of the invention.

An array 203 of detectors incorporated in one embodiment of the invention is illustrated schematically in FIG. 11a of the drawings. In this embodiment, the array comprises a strip of EMATs arranged in a generally linear relationship. The strip of EMATs is located proximal to the surface 206 of the can 201, above the surface portion 205, such that a generally planar surface 209 of the strip lies generally tangentially to the surface 206 of the can and generally perpendicular to the propagation axis 210 of the focused laser beam, as illustrated in FIG. 10. The strip of EMATs can thus detect a Lamb wave in the wall of the can, at a series of heights above the base of the can. Each EMAT generates an electrical signal dependent upon the amplitude of the Lamb wave which is detected. The electrical signals from the EMATs are input to the signal processing means 204 which comprises a personal computer (PC) programmed to analyse the electrical signals in order to determine the fill level of the liquid contents inside the container.

Figure 11B:
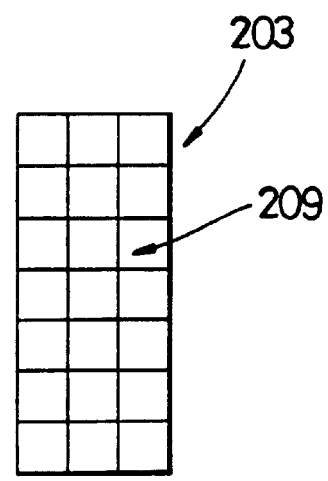
FIG. 11b is a schematic illustration of an ultrasonic wave detector array incorporated in a non-contact fill level monitoring means according to another embodiment of the invention.
Figure 12:
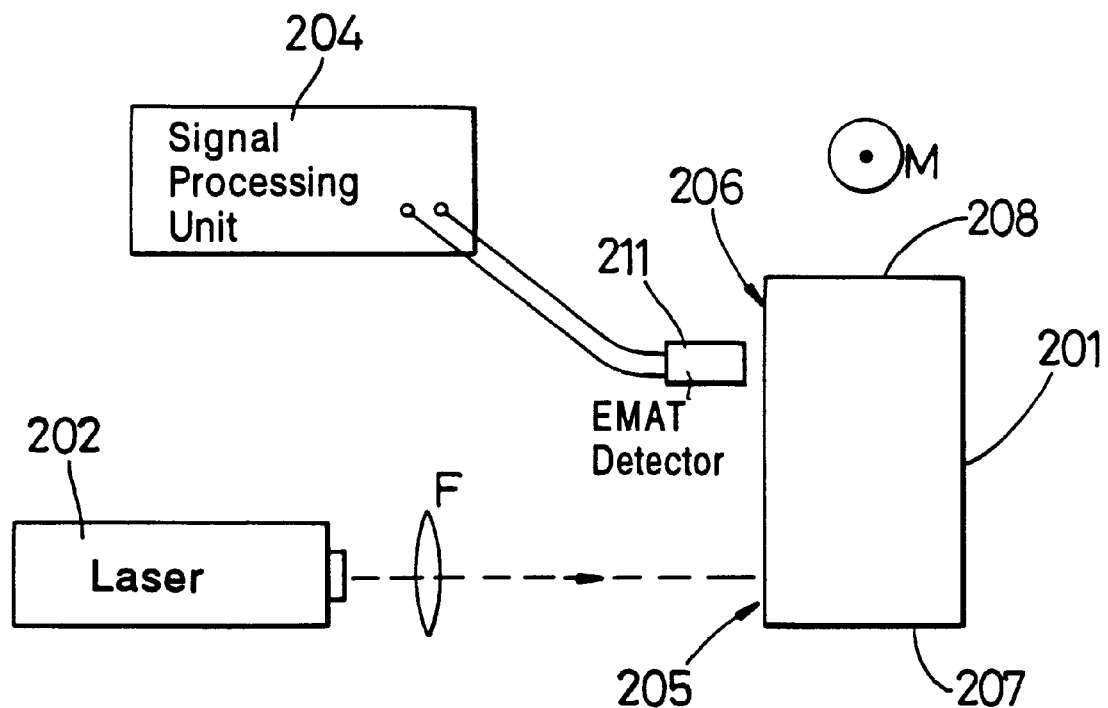
FIG. 12 is a schematic illustration of a side view of a container fill level detector according to an embodiment of the invention, in use.

An alternative array 203 of detectors incorporated in an alternative embodiment of the invention is illustrated in FIG. 11b. This array comprises a two-dimensional array of EMATs arranged in rows and columns to creates a generally planar, rectangular detecting surface 209. The detecting surface 209 is arranged, in use, generally tangentially to the surface 206 of the can 201, above the surface portion 205, and generally perpendicularly to the propagation axis 210 of the focused laser beam. In this arrangement, the array can be used to detect a Lamb wave in a larger portion of the wall of the can than is possible using the strip detector array. This advantage can be exploited to obtain a more accurate estimate of the fill level by taking an average of the electrical signals from detectors positioned at equal heights, relative to the base 207 of the can.

In the embodiment illustrated in FIG. 11, the non-contact monitoring means is operable as a non-contact container fill level detector. Instead of the array 203 of detectors, the monitoring means incorporates a single EMAT detector 211 positioned proximal (up to approximately 5 mm) to the surface 206 of the can, generally vertically above the surface portion 205, at a predetermined height above the base 207 of the can 201. The single EMAT generates an electrical signal dependent upon the amplitude of a Lamb wave it detects in the can wall, at the predetermined height. The electrical signal is input to the signal processing unit 204 which compares the signal with a predetermined reference signal (pre-programmed into a memory of the processing unit 204) in order to determine whether the can is filled to the predetermined height, with liquid contents.

It will be appreciated that "non-contact" means, in the context, non-mechanical contact, or non liquid coupling. Complaint free might be an alternative phraseology.

We claim:

1. A non-contact apparatus for monitoring contents of a moving container comprising non-contact ultrasonic wave generation means adapted to produce in use an ultrasonic wave in a container being monitored, the wave generation means comprising plasma-producing means adapted to produce a plasma at or near the surface of the container, non-contact ultrasonic wave detector means adapted to detect an ultrasonic signal and to generate a detection signal dependent upon the ultrasonic signal which is detected, and signal processing means adapted to process the detection signal generated by the ultrasonic wave detector means in order to detect a particular characteristic of the contents of the container.

2. The apparatus according to claim 1, wherein said plasma is generated at a region close to the container, but not actually on the wall of the container.

3. The apparatus according to claim 1, wherein spaced plasma generation means is provided.

4. The apparatus according to claim 3, wherein said spaced plasma generations means comprises a target that is not the container.

5. The apparatus according to claim 1, wherein said non-contact wave generation means comprises a laser.

6. The apparatus according to claim 5, which is adapted to produce a beam of laser radiation and direct it, in use, onto a container being monitored.

7. The apparatus according to claim 6, wherein said laser is a pulsed laser.

8. The apparatus according to claim 1, wherein said wave generation means is adapted to generate a wave in a moving container.

9. The apparatus according to claim 8, wherein said detector means is adapted to detect a signal in a moving container.

10. The apparatus according to claim 1, wherein said wave detector means is adapted to detect an ultrasound signal that has propagated through the contents of the container.

11. Apparatus according to claim 1, which is adapted to detect a surface wave in the container.

12. The apparatus according to claim 1, which further comprises focusing means adapted to focus a beam of laser radiation (or other energy source) to a spot on an outer surface of a first position of the container in order to generate an ultrasonic wave in said container (or focus the beam onto a plasma-generating target).

13. The apparatus according to claim 1, wherein said wave generation means comprises a laser, or plasma producing means, adapted to impinge on the container generally normal to the surface of the container.

14. Apparatus according to claim 1, wherein said wave generation means is adapted to produce ultrasound at a first portion of a container, and in which the detector means is positioned such that it detects an ultrasonic wave in a second portion of the container opposite said first portion.

15. The apparatus according to claim 1, wherein said wave generation means is adapted to produce ultrasound at a first portion of the container and said detector means is positioned such that it detects an ultrasonic wave in the first portion of the container, or a portion of the container proximal to the first portion, which wave has been reflected from other portions of the container and has propagated back to the first portion of the container, or the portion proximal to the first portion.

16. The apparatus according to claim 1, wherein said signal processing means processes the detection signals so as to determine whether the container is filled with contents at least to a predetermined level.

17. The apparatus according to claim 16, which is adapted to function as a fill level detector.

18. The apparatus according to claim 1, which is adapted to function as a means for detecting the presence, or absence, of a insert within a liquid-containing beverage can.

19. Apparatus according to claim 1, wherein said non-contact wave generation means comprises an electrical source.

20. Apparatus according to claim 1, wherein said detector means is an electromagnetic acoustic transducer (EMAT).

21. A container filling line comprising a filling station; conveyor means for moving containers past the filling station; inspection means including non-contact monitoring means; and control means; the arrangement being such that said control means controls in use the operation of said filling line in response to signals from said monitoring means, and wherein said monitoring means comprises apparatus according to claim 1.

22. The container filling line according to claim 21, which further comprises container rejection means arranged such that said control means controls in use the operation of said container rejection means in response to signals from said monitoring means so as to remove containers assessed by control means to be not acceptable.

23. The container filling line according to claim 21, which has marking means adapted to mark said container with a mark dependent upon the signals received.

24. The container filling line according to claim 21, wherein said control means also controls the filling of a container at the filling station and/or the speed of the conveyor means.

25. The container filling line according to claim 21, in which there is feedback from the monitoring means to the control means which is used to control the filling of the containers.

26. A non-contact method of monitoring the contents of a moving container comprising, firstly, generating an ultrasonic wave within a portion of said container using plasma-producing means, secondly, detecting an ultrasonic signal in a portion of said container and producing a detection signal dependent upon the detected ultrasonic signal, and thirdly processing the detecting signal in order to detect a particular characteristics of the contents of said container.

27. A method according to claim 26, which comprises the step of allowing the ultrasonic wave generated to propagate through the contents of the container before it is detected.

28. A non-contact apparatus for monitoring contents of a moving container comprising non-contact ultrasonic wave generation means adapted to produce in use an ultrasonic wave in a container being monitored, non-contact ultrasonic wave detector means adapted to detect an ultrasonic signal and to generate a detection signal dependent upon the ultrasonic signal which is detected, and signal processing means adapted to process the detection signal generated by the ultrasonic wave detector means in order to detect a particular characteristic of the contents of the container, the characteristic being whether the container is filled with contents at least to a predetermined level.

29. A non-contact apparatus for monitoring contents of a moving container comprising non-contact ultrasonic wave generation means adapted to produce in use an ultrasonic wave in a container being monitored, non-contact ultrasonic wave detector means adapted to detect an ultrasonic signal and to generate a detection signal dependent upon the ultrasonic signal which is detected, and signal processing means adapted to process the detection signal generated by the ultrasonic wave detector means in order to detect a particular characteristic of the contents of the container, the apparatus being adapted to function as a means for detecting the presence, or absence, of an insert within a liquid-containing beverage can.

30. A non-contact, non-fluid-coupled apparatus for monitoring contents of a moving container comprising non-contact, ultrasonic wave generation means adapted to produce in use an ultrasonic wave in a container being monitored, non-contact, non-fluid-coupled ultrasonic wave detector means adapted to detect an ultrasonic signal and to generate a detection signal dependent upon the ultrasonic signal which is detected, and signal processing means adapted to process the detection signal generated by the ultrasonic wave detector means in order to detect a particular characteristic of the contents of the container.

31. A non-contact apparatus for monitoring contents of a moving container comprising non-contact ultrasonic wave generation means adapted to produce in use an energy transmission of a first kind which is transformed in the container to an energy transmission of a second kind, in which the energy transmission of the second kind is an ultrasonic wave, and the energy transmission of the first kind is different from an ultrasonic wave, and non-contact ultrasonic wave detector means adapted to detect an ultrasonic signal and to generate a detection signal dependent upon the ultrasonic signal which is detected, and signal processing means adapted to process the detection signal generated by the ultrasonic wave detector means in order to detect a particular characteristic of the contents of the container.

32. A non-contact apparatus for monitoring contents of a container comprising non-contact ultrasonic wave generation means adapted to produce in use an ultrasonic wave in a container being monitored, non-contact ultrasonic wave detector means adapted to detect an ultrasonic signal and to generate a detection signal dependent upon the ultrasonic signal which is detected, and signal processing means adapted to process the detection signal of the contents of the container, the characteristic being whether the container is filled with contents at least to a predetermined level.

33. A non-contact couplant-free apparatus for monitoring contents of a container comprising non-contact ultrasonic wave generation means adapted to produce in use an ultrasonic wave in a container being monitored, non-contact couplant-free ultrasonic wave detector means adapted to detect an ultrasonic signal and to generate a detection signal dependent upon the ultrasonic signal which is detected, and signal processing means adapted to process the detection signal generated by the ultrasonic wave detector means in order to detect a particular characteristic of the contents of the container.

34. A non-contact apparatus for monitoring contents of a container comprising non-contact ultrasonic wave generation means adapted to produce in use an energy transmission of a first kind which is transformed in the container to an energy transmission of a second kind, in which the energy transmission of the second kind is an ultrasonic wave, and the energy transmission of the first kind is different from an ultrasonic wave, and non-contact ultrasonic wave detector means adapted to detect an ultrasonic signal and to generate a detection signal dependent upon the ultrasonic signal which is detected, and signal processing means adapted to process the detection signal generated by the ultrasonic wave detector means in order to detect a particular characteristic of the contents of the container.

35. Apparatus according to claim 34, wherein the energy transmission of the first kind is an electrical energy transmission.

* * * * *